(12) United States Patent
Ravikumar

(10) Patent No.: US 8,313,507 B2
(45) Date of Patent: *Nov. 20, 2012

(54) MINIMALLY INVASIVE RAKE RETRACTOR AND METHOD FOR USING SAME

(75) Inventor: Sundaram Ravikumar, Briarcliff Manor, NY (US)

(73) Assignee: Mini-Lap Technologies, Inc., Dobbs Ferry, NY (US)

( * ) Notice: Subject to any disclaimer, the term of this patent is extended or adjusted under 35 U.S.C. 154(b) by 890 days.

This patent is subject to a terminal disclaimer.

(21) Appl. No.: 11/654,970

(22) Filed: Jan. 18, 2007

(65) Prior Publication Data

US 2007/0213595 A1 Sep. 13, 2007

Related U.S. Application Data

(63) Continuation-in-part of application No. 11/420,927, filed on May 30, 2006, now Pat. No. 7,766,937.

(60) Provisional application No. 60/828,916, filed on Oct. 10, 2006.

(51) Int. Cl.
*A61B 17/00* (2006.01)

(52) U.S. Cl. ........................................ 606/205

(58) Field of Classification Search .......... 606/205–207, 606/167, 170, 185; 604/164.01, 106; D24/143
See application file for complete search history.

(56) References Cited

U.S. PATENT DOCUMENTS

| | | | |
|---|---|---|---|
| 3,817,251 A | 6/1974 | Hasson | |
| 3,844,291 A | 10/1974 | Moen | |
| 3,938,527 A | 2/1976 | Rioux et al. | |
| 3,967,625 A * | 7/1976 | Yoon | 128/831 |
| 4,016,881 A | 4/1977 | Rioux et al. | |
| 4,077,412 A | 3/1978 | Moossun | |
| 4,174,715 A * | 11/1979 | Hasson | 606/206 |
| 4,570,642 A | 2/1986 | Kane et al. | |
| D293,470 S | 12/1987 | Adler | |
| 5,073,169 A | 12/1991 | Raiken | |
| 5,100,402 A | 3/1992 | Fan | |
| 5,147,316 A | 9/1992 | Castillenti | |
| 5,176,643 A | 1/1993 | Kramer et al. | |
| 5,176,697 A | 1/1993 | Hasson et al. | |
| 5,201,742 A | 4/1993 | Hasson | |
| 5,222,973 A | 6/1993 | Sharpe et al. | |
| 5,224,954 A | 7/1993 | Watts et al. | |
| 5,290,276 A | 3/1994 | Sewell, Jr. | |
| 5,330,497 A | 7/1994 | Freitas et al. | |
| 5,342,357 A | 8/1994 | Nardella | |

(Continued)

OTHER PUBLICATIONS

Cauterization, Wikipedia entry, Mar. 14, 2008 (4 pages).

*Primary Examiner* — Ryan Severson
*Assistant Examiner* — Jonathan W Miles
(74) *Attorney, Agent, or Firm* — Gordon & Jacobson, PC

(57) ABSTRACT

A rake retractor for use in minimally invasive medical procedures such as laparoscopic surgery includes a handle shaft, rake prongs, and end configurations that can be used to move elements within a body cavity. The prongs of the rake retractor are biased to an open position such that when the rake prongs extend out of the needle they open, and they are closed by relative movement of the needle over them. The end configurations are offset so that they may be compactly brought together within the narrow space of a needle having a diameter typically not greater than 2.5 mm.

15 Claims, 9 Drawing Sheets

U.S. PATENT DOCUMENTS

| | | | |
|---|---|---|---|
| 5,354,283 A | 10/1994 | Bark et al. | |
| 5,375,588 A | 12/1994 | Yoon | |
| 5,417,697 A | 5/1995 | Wilk et al. | |
| 5,425,357 A | 6/1995 | Moll et al. | |
| 5,439,476 A | 8/1995 | Frantzides | |
| 5,527,264 A | 6/1996 | Moll et al. | |
| 5,556,411 A | 9/1996 | Taoda et al. | |
| 5,578,030 A | 11/1996 | Levin | |
| 5,613,937 A | 3/1997 | Garrison et al. | |
| 5,618,306 A | 4/1997 | Roth et al. | |
| 5,626,597 A | 5/1997 | Urban et al. | |
| 5,634,918 A | 6/1997 | Richards | |
| 5,658,272 A | 8/1997 | Hasson | |
| D388,515 S | 12/1997 | Bookwalter et al. | |
| D389,242 S | 1/1998 | Bookwalter et al. | |
| D389,913 S | 1/1998 | Bookwalter et al. | |
| 5,803,902 A | 9/1998 | Sienkiewicz et al. | |
| 5,813,976 A | 9/1998 | Filipi et al. | |
| 5,823,945 A | 10/1998 | Moll et al. | |
| 5,846,191 A | 12/1998 | Wells et al. | |
| 5,857,999 A | 1/1999 | Quick et al. | |
| 5,871,453 A | 2/1999 | Banik et al. | |
| 5,893,873 A | 4/1999 | Rader et al. | |
| 5,906,620 A | 5/1999 | Nakao et al. | |
| 5,919,163 A | 7/1999 | Glickman | |
| 5,951,488 A | 9/1999 | Slater et al. | |
| 5,951,574 A | 9/1999 | Stefanchik et al. | |
| D426,883 S | 6/2000 | Berman et al. | |
| 6,090,042 A | 7/2000 | Rullo et al. | |
| 6,099,550 A | 8/2000 | Yoon | |
| 6,155,439 A | 12/2000 | Draughn | |
| 6,165,184 A | 12/2000 | Verdura et al. | |
| 6,190,311 B1 | 2/2001 | Glines et al. | |
| 6,197,002 B1 | 3/2001 | Peterson | |
| 6,200,263 B1 | 3/2001 | Person | |
| 6,248,062 B1 | 6/2001 | Adler et al. | |
| 6,258,107 B1 | 7/2001 | Balazs et al. | |
| 6,319,266 B1 | 11/2001 | Stellon et al. | |
| 6,322,578 B1 | 11/2001 | Houle et al. | |
| 6,391,046 B1 | 5/2002 | Overaker et al. | |
| 6,428,503 B1 | 8/2002 | Kierce | |
| 6,504,985 B2 | 1/2003 | Parker et al. | |
| 6,610,009 B2 | 8/2003 | Person | |
| 6,616,683 B1 | 9/2003 | Toth et al. | |
| 6,630,103 B2 | 10/2003 | Martin et al. | |
| 6,648,839 B2 | 11/2003 | Manna et al. | |
| 6,736,814 B2 | 5/2004 | Manna et al. | |
| 6,743,237 B2 | 6/2004 | Dhindsa | |
| 6,761,718 B2 | 7/2004 | Madsen | |
| 6,830,578 B2 | 12/2004 | O'Heeron et al. | |
| 6,832,984 B2 | 12/2004 | Stelzer et al. | |
| 6,860,894 B1 | 3/2005 | Pittman | |
| 6,902,536 B2 | 6/2005 | Manna et al. | |
| 6,908,454 B2 | 6/2005 | McFarlane | |
| 6,945,984 B2 | 9/2005 | Arumi et al. | |
| 6,989,003 B2 | 1/2006 | Wing et al. | |
| 7,001,333 B2 | 2/2006 | Hamel et al. | |
| 7,041,055 B2 | 5/2006 | Young et al. | |
| 7,066,879 B2 | 6/2006 | Fowler et al. | |
| 7,112,172 B2 | 9/2006 | Orban, III et al. | |
| 7,169,156 B2 * | 1/2007 | Hart | 606/144 |
| 7,223,267 B2 | 5/2007 | Isola et al. | |
| 2001/0056286 A1 | 12/2001 | Etter et al. | |
| 2003/0040773 A1 | 2/2003 | Arumi et al. | |
| 2003/0050613 A1 * | 3/2003 | Hammerslag | 604/290 |
| 2003/0130693 A1 * | 7/2003 | Levin et al. | 606/205 |
| 2003/0145865 A1 | 8/2003 | Sterman et al. | |
| 2005/0113737 A1 | 5/2005 | Ashby et al. | |
| 2005/0273133 A1 | 12/2005 | Shluzas et al. | |

* cited by examiner

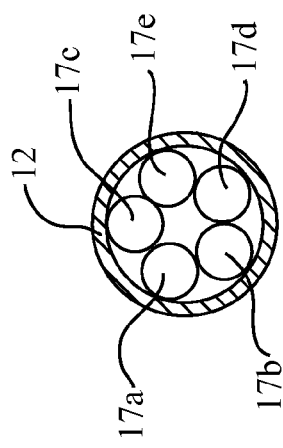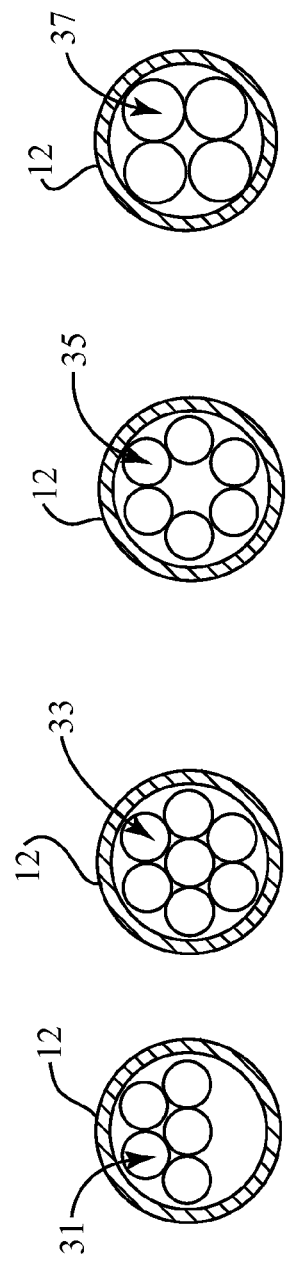

MINIMALLY INVASIVE RAKE RETRACTOR AND METHOD FOR USING SAME

This application claims the benefit of provisional application No. 60/828,916, filed Oct. 10, 2006, and is a continuation-in-part of U.S. application Ser. No. 11/420,927 filed May 30, 2006, now U.S. Pat. No. 7,766,937, both of which are incorporated herein in their entireties.

BACKGROUND OF THE INVENTION

1. Field of the Invention

The present invention relates generally to surgical instruments and methods of their use, and, more particularly, to minimally invasive surgical instruments incorporating a needle and a retractor that can be extended through and beyond the needle and which can be retracted into the needle. The present invention has particular application to laparoscopic-type surgery, although it is not limited thereto.

2. Background Information

Over the last two decades, minimally invasive surgery has become the standard for many types of surgeries which were previously accomplished through open surgery. Minimally invasive surgery generally involves introducing an optical element (e.g., laparoscope or endoscope) through a surgical or natural port in the body, advancing one or more surgical instruments through additional ports or through the endoscope, conducting the surgery with the surgical instruments, and withdrawing the instruments and scope from the body. In laparoscopic surgery, a port for a scope is typically made using a surgical trocar assembly. The trocar assembly often includes a port, a sharp pointed element (trocar) extending through and beyond the distal end of the port, and at least in the case of abdominal laparoscopy, a valve on the proximal portion of the port. Typically, a small incision is made in the skin at a desired location in the patient. The trocar assembly, with the trocar extending out of the port is then forced through the incision, thereby widening the incision and permitting the port to extend through the incision, past any facie, and into the body (cavity). The trocar is then withdrawn, leaving the port in place. In certain circumstances, an insufflation element may be attached to the trocar port in order to insufflate the surgical site. An optical element may then be introduced through the trocar port. Additional ports are then typically made so that additional laparoscopic instruments may be introduced into the body.

Trocar assemblies are manufactured in different sizes. Typical trocar port sizes include 5 mm, 10 mm and 12 mm (available from companies such as Taut and U.S. Surgical), which are sized to permit variously sized laparoscopic instruments to be introduced therethrough including, e.g., graspers, dissectors, staplers, scissors, suction/irrigators, clamps, forceps, biopsy forceps, etc. While 5 mm trocar ports are relatively small, in some circumstances where internal working space is limited (e.g., children), it is difficult to place multiple 5 mm ports in the limited area. In addition, 5 mm trocar ports tend to limit movements of instruments inside the abdominal cavity to a great extent and, while relatively small, still leave holes that must be stitched and still result in undesired scarring.

One type of laparoscopic instrument used by surgeons is the retractor, which may be used for moving or manipulating body cavity tissue, particulate matter, and/or debris, where such uses may include retracting contents of the abdominal cavity, like the small bowel, stomach, colon. Available laparoscopic retractors include the retractable rake retractors. As an example, U.S. Pat. No. 6,743,237 to Dhindsa describes an endoscopic instrument having an extendable wire and also a collapsible rake element.

There remains, however, a need for further advancements in minimally invasive surgical instruments and procedures, and particularly, a need for a minimally invasive retractor instrument.

SUMMARY OF THE INVENTION

Various embodiments of the present invention provide a minimally invasive rake retractor, a surgical apparatus comprising the rake retractor, and a surgical method using the minimally invasive rake retractor, that do not require the surgeon to make an initial incision for inserting the retractor, and that do not require stitching of the hole or wound resulting from the inserting the surgical apparatus into a body cavity, and that result in insignificant scarring compared to scarring resulting from using known laparoscopic retractors and other instruments.

In accordance with some embodiments of the present invention, a surgical assembly comprises (i) a hollow needle having a sharp distal end operative in puncturing skin to insert and advance the surgical instrument into the body, and having an outer diameter dimensioned such that a wound formed from the hollow needle puncturing the skin is capable of being closed independent of stitching; and (ii) a surgical instrument having a shaft that extends through said hollow needle, said surgical instrument being movable relative to said hollow needle and including at a distal end of said shaft a plurality of elongated members, each elongated member having a first end mechanically coupled to the distal end of the shaft and an opposite free end, each elongated member being mechanically biased such that when said elongated members extend externally to said needle into an open position said elongated members automatically expand relative to each other, and when said hollow needle extends over said elongated members in a closed position, said elongated members are forced to collapse relative to each other against the mechanical bias.

The surgical assembly may also include a fixing means coupled to said surgical instrument and said hollow needle for fixing said surgical instrument relative to said needle. In some implementations, the outer diameter of the needle may be substantially 2.5 mm or smaller.

The elongated members, also referred to hereinbelow as tines or prongs, may have various configurations. In some implementations, at least one of the tines is mechanically biased such that when the tines are extended externally to said needle, each of these mechanically biased tines automatically mechanically relaxes to provide a curvature over at least a portion of the tine. The curvature may be continuously arcuate, independent of angular bends, or may include one or more bends along with straight segments and/or curved segments. The free ends of the elongated members may be blunted. For instance, the free ends may include ball-tips or spoon-shaped elements. In some implementations, when in the closed position, the distal ends of at least two of said elongated members are displaced longitudinally along the length of said needle.

In some embodiments of the invention, the shaft is mechanically biased over at least a portion thereof such that when the portion of the shaft is extended externally to said needle, the shaft automatically mechanically relaxes to provide a curvature over at least the portion of the shaft. The mechanical bias may be provided by at least one bend in said shaft.

In accordance with various embodiments of the present invention, a rake retractor for use in a minimally invasive surgical broadly includes a shaft coupled to a plurality of free ends. The free ends at the end of the shaft are biased to an open position. When the free ends extend outside the needle, they open, and they are closed by relative movement of the needle over them.

The prongs of the rake retractor may be affixed to the rake shaft by a simple weld or mechanical fixing mechanism. Alternatively, the prongs may be extensions of the shaft itself. The prongs themselves may be straight or have a variety of free end configurations. For example, the prongs may have one or more bends to assist the surgeon on reaching obstructed areas or the prong may be fitted with ball tips or tool-like structural configurations. Similarly, the prongs may have an arcuate shape whereby they form a curvature.

The rake retractor according to embodiments of the invention may be used through a laparoscopic surgical instrument in a variety of configurations. In particular, the rake retractor may have ball-shaped or spoon-like configurations to assist the surgeon in moving material found below the skin surface. These blunted configurations guard against the possibility of the surgeon pressing the instrument too hard against an internal body organ and the risk of puncture.

Furthermore, the rake retractor according to embodiments of the invention is designed so that it can be easily positioned through a laparoscopic needle. The rake retractor prongs remain bunched inside the needle in a collapsed position until the surgeon moves the retractor and needle relative to each other such that the retractor extends outside the distal end of the needle. When this extension occurs, the rake prongs are biased to an open position so that they automatically spread relative to each other into an expanded position as the prongs leave the interior of the needle. Similarly, when the surgeon moves the needle and retractor relative to each other such that the retractor is withdrawn back into the needle, the prongs progressively return to a collapsed position against their opening bias.

In various embodiments, the free ends of the rake prongs are positionally offset relative to one another so that when engaged to return to the collapsed position, the free ends do not simultaneously occupy the same lateral space. This offset feature allows the free ends of the rake prongs to be provided with end configurations of a size which would otherwise be unable to fit within the narrow confines of a laparoscopic needle or other passage when the prongs are in the collapsed position. Preferably, this offset feature is achieved by terminating the prongs (with or without attached free end configurations) at different positions relative to the longitudinal axis of the retractor shaft. It is not necessary that every rake prong is offset from the others; rather, it is important that enough rake prongs are offset so that the collapsed position inside the needle can be realized.

According to various embodiments of the present invention, a locking mechanism is provided allowing the surgeon to have the ability to affix the rake retractor in a position relative to the needle. According to some such embodiments, the locking means selectively affixes the shaft of the retractor to a position along the interior of the needle. This locking means may include a large number of mechanical embodiments such as screwing mechanisms, detent mechanisms, and peg-notch junctions, to name a few.

It will be appreciated by those skilled in the art that the foregoing brief description and the following detailed description are exemplary and explanatory of this invention, but are not intended to be restrictive thereof or limiting of the advantages which can be achieved by this invention. Additionally, it is understood that the foregoing summary of the invention is representative of some embodiments of the invention, and is neither representative nor inclusive of all subject matter and embodiments within the scope of the present invention. Thus, the accompanying drawings, referred to herein and constituting a part hereof, illustrate embodiments of this invention, and, together with the detailed description, serve to explain principles of this invention.

BRIEF DESCRIPTION OF THE DRAWINGS

Aspects, features, and advantages of embodiments of the invention, both as to structure and operation, will be understood and will become more readily apparent when the invention is considered in the light of the following description made in conjunction with the accompanying drawings, in which like reference numerals designate the same or similar parts throughout the various figures, and wherein:

FIG. 2E is a schematic cross-sectional view of the distal end of the surgical apparatus with the rake retractor in the fully retracted position, viewed along the longitudinal axis as indicated by reference lines III-III' in FIG. 2A, in accordance with some embodiments of the present invention;

FIGS. 3A-3D are schematic cross-sectional views of the distal end of the surgical apparatus in accordance with various alternative tine configurations, viewed from a perspective corresponding to that of FIG. 2E, in accordance with various embodiments of the present invention;

DETAILED DESCRIPTION OF EMBODIMENTS OF THE INVENTION

Figure 1A:
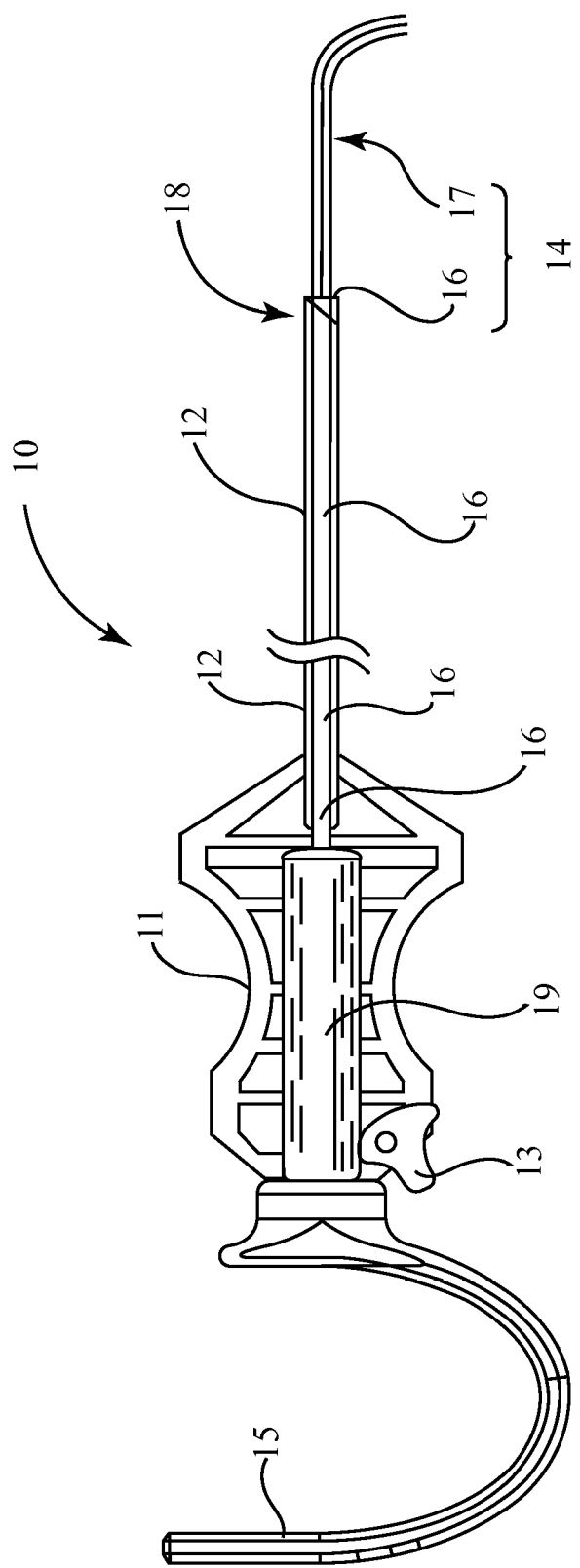
FIG. 1A is a schematic cross-sectional view of proximal and distal portions of a surgical assembly comprising a rake retractor, in accordance with an embodiment of the present invention.
Figure 1B:
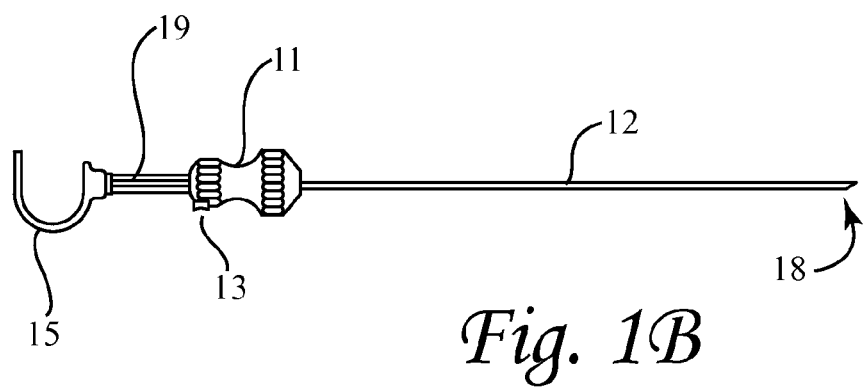
FIGS. 1B and 1C are side views of the surgical assembly of FIG. 1A, with the retractor in the retracted and extended positions, respectively, in accordance with an embodiment of the present invention.
Figure 1C:
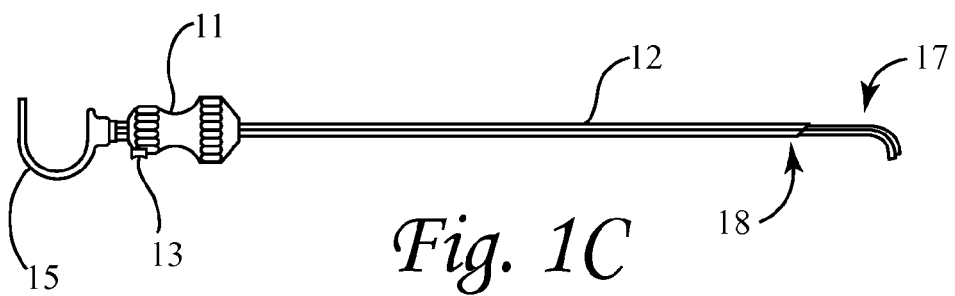

Referring now to FIGS. 1A-1C, shown is a minimally invasive surgical assembly 10 comprising a rake retractor 14 according to an illustrative embodiment of the present invention. More specifically, as will be further understood from the ensuing description, FIG. 1A is a schematic cross-sectional view of proximal and distal portions of surgical assembly 10 with rake retractor 14 in an extended position, and FIGS. 1B and 1C are side views of surgical assembly 10 with the retractor 14 in the retracted and extended positions, respectively. As depicted, surgical assembly 10 includes outer hollow needle 12; a grip 11 attached to a proximal portion of outer needle 12 and having a locking mechanism 13; rake retractor 14 comprising a shaft 16 that extends coaxially through the outer hollow needle 12 and retractor tines 17 at the distal end of the shaft; a handle 15 mechanically coupled to a proximal shaft 19 that is mechanically coupled to the proximal end of shaft 16. As will be further understood hereinbelow, retractor 14 may be moved longitudinally (i.e., in the direction of the coaxial axis) relative to outer hollow needle 12 such that retractor tines 17 may be fully retracted within outer hollow needle 12 (e.g., as shown in FIG. 1B) or partially or fully extended out of the outer hollow needle 12 (e.g., as shown in FIG. 1C). Additionally, locking mechanism 13 may be used to selectively fix or secure retractor 14 relative to needle 12.

In accordance with various embodiments of the present invention, outer hollow needle 12 is typically between 10 and 30 cm long, and more typically between 13 and 18 cm long (although other sizes could be used, depending upon the surgery involved, and typically larger for obese patients and smaller for infants and small children), and is made from stainless steel, although other materials could be used. In this embodiment, needle 12 has a sharpened distal end 18 which is angled at about 35° relative to a longitudinal axis of the needle, and has an outer diameter of about 2 mm (about 0.079 inches or 79 mils), an inner diameter of about 1.5 mm (about 0.060 inches or 60 mils), and a wall thickness of about 0.25 mm (about 0.010 inches or 10 mils).

As will be appreciated by those skilled in the art, the outer diameter of 2 mm is sufficiently narrow such that a wound (e.g., puncture wound) formed by the needle does not require suturing or stitching, and upon healing will not result in a scar (or will not result in substantial or noticeable scarring). Those skilled in the art will further understand, however, that needle 12 may be implemented with an outer diameter larger than 2 mm (e.g., 2.5 mm or 3.0 mm or larger) while still being sufficiently narrow such that a wound formed by the needle does not require suturing or stitching and/or upon healing will not result in scarring.

Implementing needle 12 with a sufficiently narrow outer diameter and a sharpened tip also allows for inserting surgical apparatus 10 into a patient (e.g., into the abdominal cavity) by using the needle to pierce or puncture the skin and fascia without first making an incision (e.g., a cutaneous incision), though the surgeon may still choose to make an initial incision through which the needle 12 will be inserted. As will be understood and more fully appreciated from the ensuing description, while various embodiments of the present invention are configured using an outer needle having a diameter that is sufficiently narrow such that a wound (e.g., puncture wound) formed by the needle does not require suturing or stitching, alternative embodiments of the present invention may employ an outer needle or outer sleeve (e.g., which, in some embodiments, may not be configured as a needle, nor otherwise have a sharp or pointed tip) having a diameter that is greater than such a sufficiently narrow diameter (e.g., and thus, the incision or wound through which the outer needle or sleeve is inserted may require stitches or sutures). Further, in alternative embodiments of the present invention, needle 12 may be alternatively implemented as an outer sleeve that does not have a sharp or pointed tip, regardless of the outer diameter of the outer sleeve.

The embodiment of the rake retractor 14 shown in FIG. 1A, and further depicted in FIGS. 2A-2D, is a retractor type instrument having an elongated shaft 16 that is generally coaxial with the with outer needle 12 when inserted therein. As shown, in this embodiment, the proximal end of shaft 16 is mechanically coupled to a larger diameter proximal shaft 19 that is in turn mechanically coupled to a handle 15. Each such mechanical coupling may be provided in any of various common or different ways, such as by integral formation (e.g., by machining from a unitary component) or by fastening (e.g., by welding, epoxying, threading, etc.) the components directly to each other or to an intermediary coupling member. While retractor 14 includes a shaft 16 and tines 17, in some embodiments proximal shaft 19 as well as handle 15 may be considered as being part of the retractor.

As will be further understood below, in some embodiments the surgical assembly 10 may be adapted such that the retractor 14 along with mechanically coupled shaft 19 and handle 15 may be entirely disengaged from, and selectively inserted by a surgeon into, needle 12 and grip 11. Accordingly, the surgeon may insert the retractor 14 into grip 11 and needle 12 after inserting needle 12 into the patient. Additionally, the surgeon may, if desired, remove the retractor 14 and insert a different instrument into the same needle 12 that is already positioned in the patient.

In some embodiments, a guide mechanism, such as a combination of one or more longitudinal slots and one or more complementary tabs or ridges or rails provided on shaft 19 and the inner bore of grip 11, may be implemented such that retractor 14 has a fixed rotational (e.g., azimuthal) orientation about the longitudinal axis and relative to needle 12 as retractor 14 is moved along the longitudinal direction (e.g., between the fully retracted and fully extended positions). Various guide configurations may be provided such that for a given apparatus 10, the rotational (azimuthal) orientation of the retractor relative to longitudinal axis of needle 12 may be any one of two or more possible orientations that may be selected upon insertion of the retractor into the grip 11 and needle 12 (e.g., by aligning the complementary components of the guide mechanism in a desired orientation upon insertion). By way of example, shaft 19 may have two longitudinal slots displaced by 180° about the longitudinal axis, and either two rails (or two tabs) displaced by 180° about the longitudinal axis or one longitudinal rail (or a single tab) may be provided on the inner bore of grip 11, thus allowing retractor 14 to be selectively oriented in one of two azimuthal orientations (displaced by 180°) relative to the longitudinal axis of the needle 12. As may be appreciated, rather than providing guides (e.g., slots/grooves and complementary rails/tabs) to prevent free rotation of a generally cylindrically shaped shaft 16 and proximal shaft 19, inner bore of grip 11 and proximal shaft 19 may have a non-circular cross-sectional shape that permits orientation in only one or more discrete rotational orientations. For instance, a square cross section for shaft 19 and the inner bore of grip 11 would permit retractor 14 to be orientated in any one of four rotational positions about the longitudinal axis associated with needle 12. In various alternative embodiments, such guides may provide for some limited range of rotation about the longitudinal axis (e.g., the circumferential width of the slot compared to the width of the tab or rail may allow for 30° or 45° rotation about the longitudinal axis). In yet other embodiments, such guide mechanisms may not be provided, or may be disengaged, such that the retractor 14 may be freely rotated by the surgeon about the longitudinal axis to manipulate and position the retractor at any desired azimuthal angle.

According to various embodiments of the invention, the retractor 14 and needle 12 are sized so that at least a portion of the shaft 16 of the retractor 14 interferingly slides against the inner surface of the needle 12, thereby forming a seal which is effective against desufflation. Thus, in the illustrative embodiment, the outer diameter of the shaft 16 is approximately 1.49 mm (0.059 inches or 59 mils), or about 0.01 mm smaller than the inner diameter of the needle. This small difference in diameters results in a sliding interference fit which can be felt as a drag and which effectively acts as a seal against desufflation. Alternatively or additionally, the needle may include an internal gasket or seal (e.g., an O-ring) that seals against the outer diameter of the shaft. In various embodiments, a seal against desufflation may additionally or alternatively be provided between at least a portion of shaft 19 and the inner bore of grip 11.

Figure 2A:
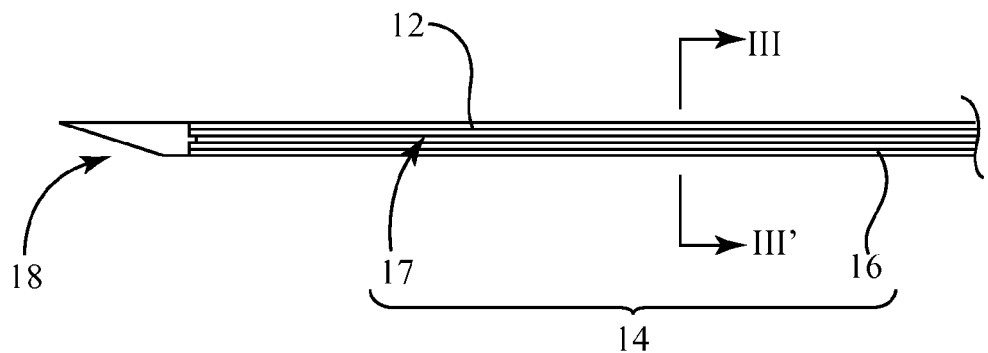
FIG. 2A depicts a schematic side sectional view of the distal portion of a needle with a rake retractor in a closed position such that the tines of the rake retractor or fully enclosed within the needle, in accordance with an embodiment of the present invention.
Figure 2B:
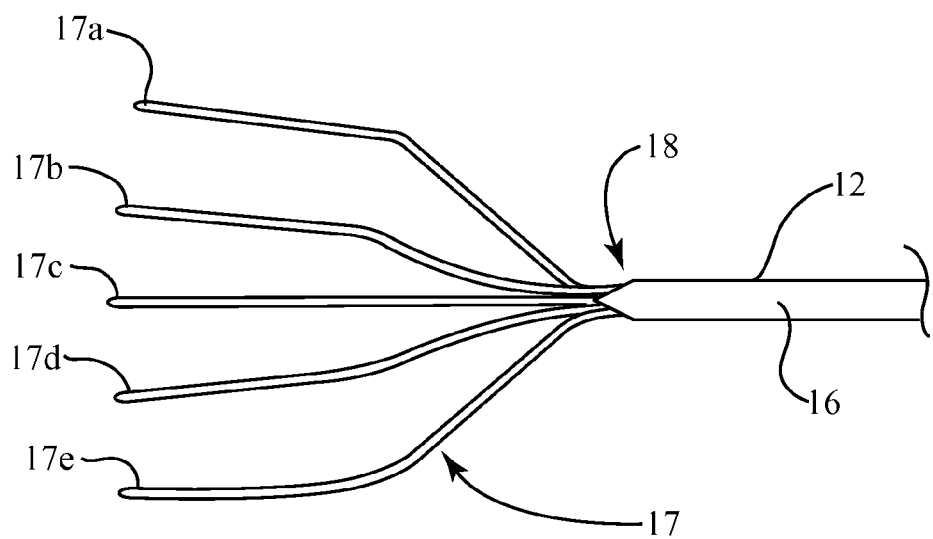
FIG. 2B depicts a plan view from above, according to the orientation of the side views of FIGS. 1A-1C and 2A, of the distal portion of the needle with the rake retractor in an opened position such that the tines of the rake retractor are expanded, in accordance with an embodiment of the present invention.
Figure 2C:
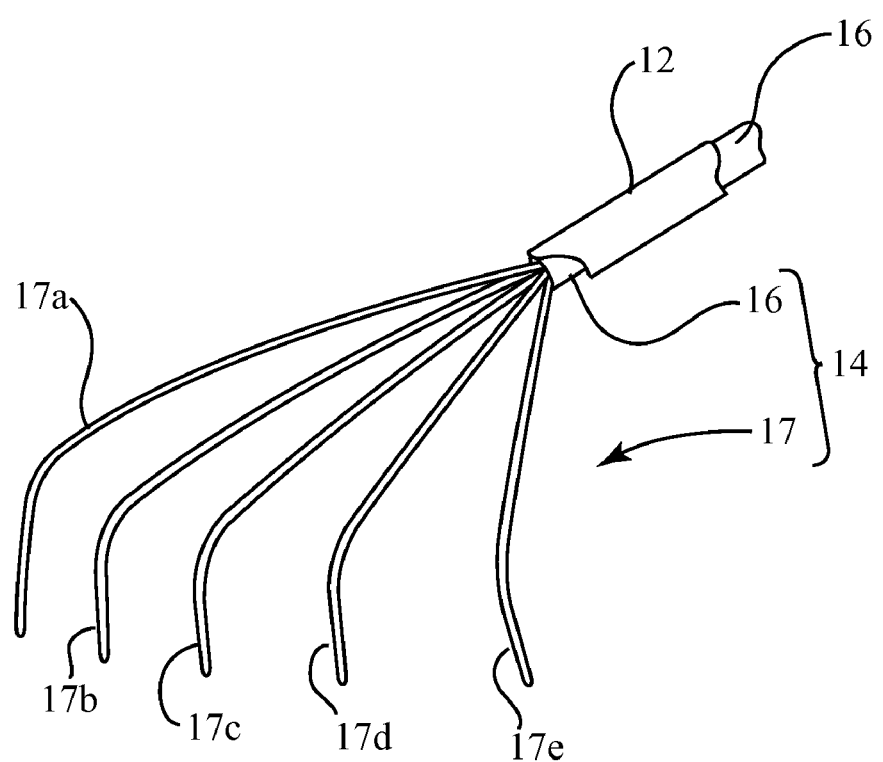
FIG. 2C illustrates a perspective view corresponding to FIG. 2B, in accordance with an embodiment of the present invention.
Figure 2D:
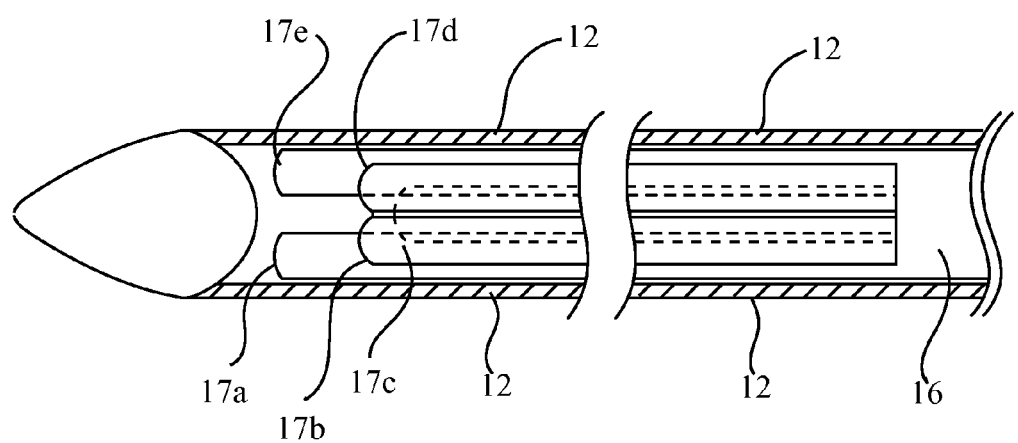
FIG. 2D depicts a schematic partial sectional view from underneath, according to the orientation of the side views of FIGS. 1A-1C and 2A, the distal portion of the needle with the rake retractor in a closed position such that the tines of the rake retractor or fully enclosed within the needle, in accordance with an embodiment of the present invention.

As depicted in FIGS. 1A and 1C, and in more detail in FIGS. 2A-2D, the distal end of retractor 14 includes tines 17, which, in this embodiment, have a curved, continuous arcuate shape. Tines 17 (i.e., comprising individual tines 17a-e) are formed so that they are mechanically biased to an open position (as seen in FIGS. 1A and 1C, and FIGS. 2B and 2C) such that they automatically open when the end effectors 22 of the surgical instrument 14 extend out of the needle 12, and they close when the needle extends over them (as seen in FIG. 1B, and FIGS. 2A and 2D). More specifically, the tines 17 are mechanically/elastically strained in the closed position (e.g., when disposed within the needle) and are under monotonically decreasing elastic strain as the tines 17 are increasingly extended out of the needle 12 (i.e., the mechanical strain decreases as the tines extend to their biased, relaxed position). The tines 17 may be formed from the end of the shaft 16, such as by machining or etching, or may be formed in any other desired manner, such as by separately forming individual tines 17 and connecting them (e.g., by welding) to the shaft. The combined length of shaft 16 and shaft 19 compared to the combined length of needle 12 and grip 11 must be long enough to permit the tines 17 to extend out of the needle. The retractor 14 is preferably made from stainless steel, although other materials could be used for all or part of the instrument 14.

As shown in FIGS. 2B and 2C, in this embodiment, when extended into the open position, tines 17 fan out relative to one another, with the proximal portions of the tines being disposed approximately in a plane that is approximately parallel with the longitudinal axis, and with the distal end portion of each tine curving along a direction that is in a plane that intersects, and in this embodiment is approximately perpendicular to, the plane in which the proximal portions of the tines fan out. As schematically depicted in FIGS. 2A and 2D, when in the closed position, tines 17 are substantially straight and parallel, packed along and within the distal portion of needle 12. In accordance with various embodiments of the present invention, the end portions are blunt or rounded (to prevent or reduce the likelihood that the tines will inadvertently puncture tissue). Additionally, as depicted in FIG. 2D, in various embodiments, the ends of two or more tines in the closed position do not occupy a common plane that is substantially perpendicular to the longitudinal axis of needle 12, although in various embodiments two or more tines may substantially occupy such a plane.

This design feature of the end portions of the tines may be provided to achieve various design objectives; for example, the end portions not occupying a common plane substantially perpendicular to the longitudinal axis may result from the tines design being provided to ensure that when the tines open they each extend approximately the same distance in the longitudinal direction before curving, and the hooked or curved portion of each tine is substantially the same shape and length. As such, under these design parameters, tines that fan out to a greater extent will be longer (assuming all tines emanate from the shaft 16 at a common plane substantially perpendicular to the longitudinal axis). It is appreciated, however, that the tines need not extend the same distance longitudinally, nor need to have the same curvature or length of their distal portions. As will be further understood below, having at least two of the end portions not occupying a common plane substantially perpendicular to the longitudinal axis may also be well suited for allowing the tips or end portions of the tines to be wider than the width or diameter of the remainder of the tines (e.g., ball tips), while allowing the tines to fit within the needle 12 (i.e., by preventing the tips, e.g., balltips, from physically interfering with each other, viz., attempting to occupy the same space within the needs, when closed).

FIG. 2E is a schematic cross-sectional view of the distal end of surgical apparatus 10 with instrument 14 in the fully retracted position, viewed along the longitudinal axis associated with outer needle 12 and coaxial shaft 16 at a longitudinal position adjacent to and distal from the longitudinal position where retractor tines 17a-e emanate from shaft 16 of retractor 14, as indicated by reference lines III-III' in FIG. 2A, in accordance with some embodiments of the present invention. As shown, in this embodiment retractor tines 17a-e have a generally equally sized circular cross-section (though they need not have equal sizes, nor must they have a uniform cross section along their length), and their respective center axes are disposed in an approximately pentagonal relationship, this pentagonal configuration providing essentially the most efficient circular cross-section tine packing within the circular inner cross-section of the needle, allowing each of the five equal-diameter tines to have essentially the largest equal diameter while fitting within the needle.

As may be appreciated, however, in various alternative embodiments, different numbers, shapes, and/or spatial configurations of tines may be employed. By way of illustrative, non-limiting examples, FIGS. 3A-3D depict cross-sectional views of various illustrative alternative tine implementations having different numbers of tines and/or spatial configurations, though the tines in each of these configurations have a generally circular cross section. More specifically, FIG. 3A depicts five tines 31 spatially configured according to a generally hexagonal close-packed arrangement, which is the arrangement also implemented to provide six tines 33 and seven tines 35 in the configurations of FIGS. 3B and 3C, respectively. FIG. 3D depicts four tines 37 spatially configured according to a generally square arrangement.

As may be appreciated from the foregoing, and as will be further understood below, the tines 17 of retractor 14 may be implemented in any of myriad configurations; for example, the number, shape, length, mechanical strength and elasticity or resiliency of the tines may be selected and designed to satisfy various uses or objectives (e.g., depending on type of surgery, type and size of tissue to be retracted, etc.). In such myriad configurations and variations, however, the tines are mechanically biased to an expanded position such that they automatically spread relative to each other when they are extended out of the needle.

Figure 4A:
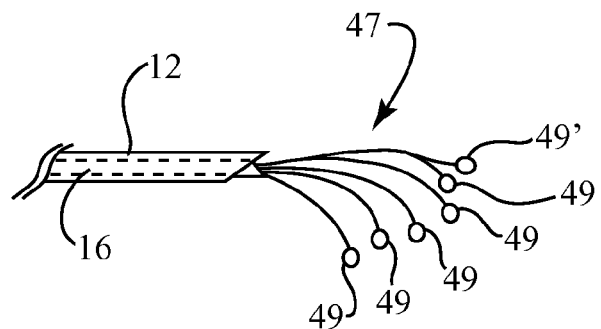
FIGS. 4A-4F schematically depict the distal portion of the surgical instrument for various configurations of the tines, in accordance with some embodiments of the present invention.
Figure 4B:
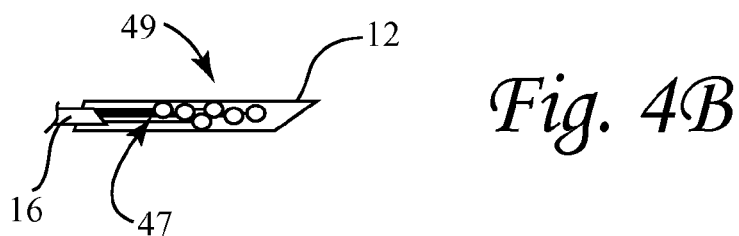

For example, referring to FIG. 4A, depicted is an embodiment of the present invention in which tines 47 include ball-tips 49. As noted above, the ball tips may be provided to help prevent tissue damage. Additionally, the ball ends may also facilitate using the rake retractor to rake, scrape, or otherwise manipulate tissue or other particulates or materials. As shown, in accordance with some embodiments, one of the tines emanating from shaft 16 may be formed into a Y-shaped distal portion, which, in this embodiment, also includes a ball tip 49 on each end. As may be appreciated, other embodiments not employing ball-ends may also be implemented with Y-shaped tines. FIG. 4B schematically depicts the tines of FIG. 4A in the closed position, with the ball tips 49 displaced longitudinally such that the tines may fit within a smaller diameter needle than otherwise would be required if the ball tips were not displaced as such and would interfere with each other. As noted above, it is not necessary for all the ball-tips to be displaced longitudinally relative to each other; a sufficient number of them should be longitudinally displaced to permit the needle diameter to be a small as desired.

Figure 4C:
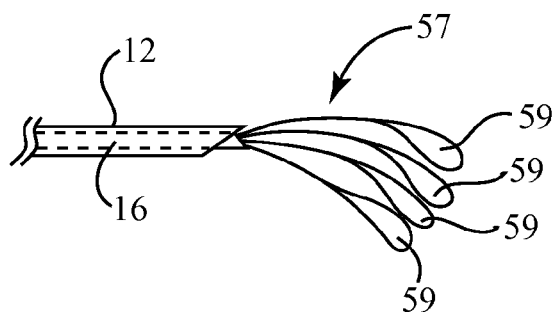

As depicted in FIG. 4C, in accordance with some embodiments, a rake retractor may have tines 57 having spoon-like shaped ends 59. Such a spoon-like shape may assist scooping or scraping various types of tissue or particulates that may be encountered during various types of surgeries. Alternatively, these elements may be used by the surgeon to assist in the placement of desired surgical tools or pharmaceutical agents. As described for the embodiment of FIGS. 4A and 4B, the tines 57 in this embodiment may be configured such that they are longitudinally displaced when in the closed position. Additionally, or alternatively, two or more of the spoon-like ends may be configured to spoon against each other when in the closed position.

Figure 4F:
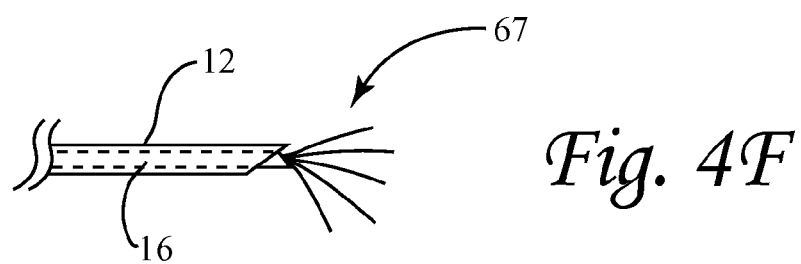
Figure 4D:
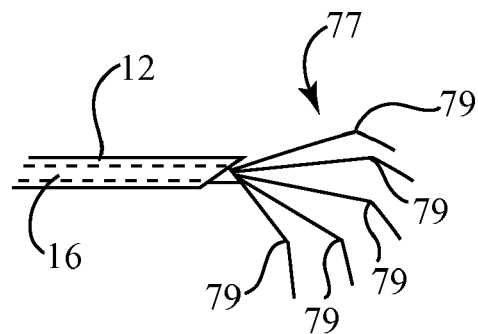
Figure 4E:
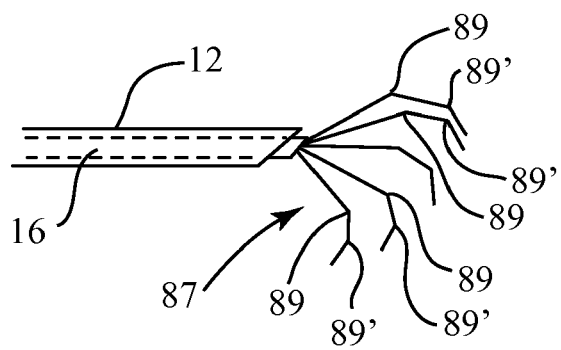

FIG. 4D schematically illustrates a rake retractor according to another embodiment of the present invention, wherein tines 77 include angular bends 79 to provide a hooked configuration. In this embodiment, tines 77 are nevertheless substantially straight and substantially aligned along the longitudinal axis when the tines 77 are entirely within needle 12 in the closed position. As depicted in FIG. 4E, each of one or more tines 87 may include two or more angular bends 89 and 89' to provide increased curvature or hooking, e.g., for greater scooping effect, which may be desired in various implementations.

While in the embodiments discussed above, the tines have a curved, hooked, or bent shape, which may facilitate using retractor 14 to pull tissue structures, in some embodiments the tines may be substantially straight, substantially without curvature or bends, such as depicted in FIG. 4F.

Figure 5A:
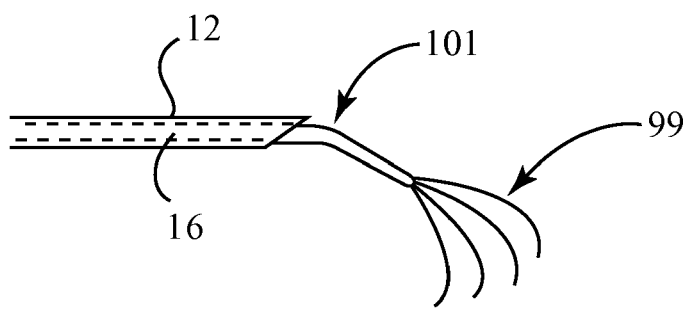
FIGS. 5A and 5B schematically depict the distal portion of the surgical instrument for various configurations of the shaft, in accordance with some embodiments of the present invention.
Figure 5B:
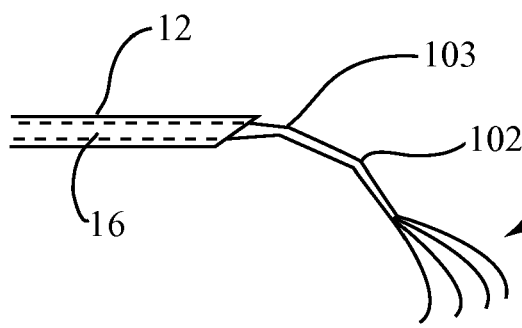

In various embodiments, shaft 16 may alternatively or additionally be adapted to provide a hooking or scooping effect. For instance, as illustrated in FIG. 5A, shaft 16 of the rake retractor (with tines 97) may include an angular bend 101 to provide a mechanical bias. Similarly, FIG. 5B illustrates a further illustrative embodiment of a rake retractor (with tines 107) with angular bends 102 and 103 along shaft 16. As may be appreciated additional bends may be provided, and the distance between bends determined according to the implementation. As may be appreciated, using such embodiments of a rake retractor, the surgeon may adjust the scooping effect by moving the shaft 16 relative to needle 12 longitudinally to selectively extend or retract one or more angular bends relative to the end of the needle. In the fully retracted position, the shaft 16 is substantially straight and substantially parallel to the longitudinal axis of the needle 12, and the shaft is in a mechanically strained condition, which is relaxed as each of the one or more angular bends are extended external to the needle. As may be appreciated, while the embodiments of FIGS. 5A and 5B illustrate using angular bends to bias shaft 16, in various implementations shaft 16 may alternatively or additionally be mechanically biased such that it has a continuous arcuate curvature along at least a portion thereof when in a mechanically relaxed state (e.g., when extended outside the needle).

A surgical apparatus 10 comprising a rake retractor 14 in accordance with embodiments of the present invention may be used by a surgeon in accordance with the following illustrative method. With the rake retractor 14 inserted in the needle 12 (e.g., with the tines withdrawn within the needle 12), the surgeon uses the needle 12 to puncture the skin and advance the needle portion of the surgical apparatus into the body (e.g., the abdomen). Alternatively, as described above, the rake retractor 14 may be inserted into the needle 12 after the needle 12 is inserted into the patient. It may also be understood that although needle 12 may be adapted to puncture the skin and penetrate the facia, the surgeon may, if desired, nevertheless make an initial incision (e.g., cutaneous incision) into which the needle is inserted. At a desired location (typically under guidance of an already inserted scope), the movement of the needle is stopped. The rake retractor 14 is then unlocked (if previously locked, e.g., by locking mechanism 13 and/or other locking mechanisms, such as a thumbscrew) and advanced relative to the needle 12 to extent the tines 17 beyond the distal end of needle 12 such that they automatically expand into the open position.

The surgeon may then lock the retractor 14 relative to needle 12 (e.g., using locking mechanism 13F), and may further move the retractor and needle together to maneuver the tines of the rake retractor 14 to manipulate tissue or other objects within the patient (e.g., within the abdominal cavity). During surgery, the surgeon may selectively unlock locking mechanism 13 and adjust the relative position of shaft 16 relative to needle 12 as desired, and then relock locking mechanism 13.

If during surgery the rake retractor is not needed, the locking mechanism 13 may be unlocked and the rake retractor 14 pulled proximally relative to needle 12 such that the tines 17 are fully retracted into needle 12. The locking mechanism 13 may then be engaged (locked). The surgical apparatus 10 may be withdrawn from the body typically, but not necessarily, with the rake retractor first withdrawn relative to the needle such that the tines are in the closed position within the needle.

In accordance with various embodiments of the present invention, removal of the surgical instrument 10 leaves a small puncture mark that will often heal without a scar. It is also noted that because of the small diameter of the surgical assembly according to various embodiments of the present invention, withdrawal of the needle assembly from the abdomen will not cause desufflation, and should not require stitching to close the wound.

As previously mentioned, the surgical apparatus 10 in accordance with various embodiments of the present invention includes a locking means that is used to fix the relative location of the rake retractor 14 relative to needle 12. In the embodiment illustrated in FIGS. 1A-C, locking mechanism 13 is provided as a cam element that is rotatingly coupled to the grip 11 by a pin 73. When in a first orientation, the cam element permits proximal shaft 19, and thus shaft 16 of retractor instrument 14 to which proximal shaft 19 is mechanically coupled (e.g., fastened to or integrally formed with) r fastened to) to move in an uninhibited manner. When in a second orientation, the cam element engages shaft 19 and holds shaft 19, and hence retractor 14, fixed relative to the grip 11 and needle 12.

Those skilled in the art will understand that any of a variety of alternative or additional locking mechanisms may be implemented, and further, that different grip and handle designs may also be implemented.

FIGS. 6A-6D schematically depict various illustrative locking mechanisms that may be additionally or alternatively implemented in accordance with some embodiments of the present invention. More specifically, in FIG. 6A, a fixing system 50 is shown to include notches 52 on at least a portion of the shaft 16 of the rake retractor instrument 14, and a screw 54 which extends through a threaded radial hole 55 in the needle 12 or its grip 11. When it is desired to fix the rake retractor 14 relative to the needle 12, the screw 54 is screwed (typically clockwise) into the needle and into engagement with a notch 52. When it is desired to release the rake retractor 14, the screw 54 is unscrewed so that it is no longer engaged in the notch. It will be appreciated that instead of a screw 54 and a threaded radial hole 55, a spring loaded pin which extends through a radial hole in the needle (or needle handle) could be utilized to lock the surgical instrument 14 relative to the needle 12. Those skilled in the art will also understand that any of a variety of detent mechanisms may be similarly employed.

Figure 6A:
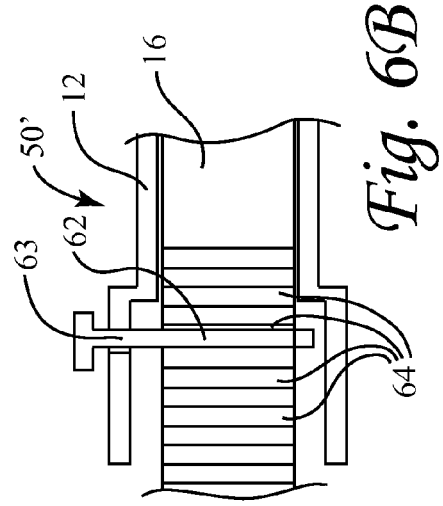
FIGS. 6A-6D schematically depict illustrative cross sectional views of various locking mechanisms that may be employed in accordance with some embodiments of the present invention.
Figure 6B:
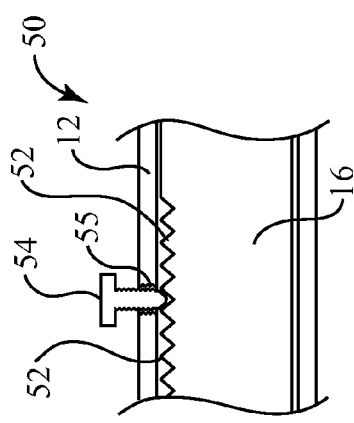

In FIG. 6B, another fixing system 50' is shown to include radial grooves 60 on the shaft 16 of the rake retractor and a clip 61 having spring arms 62 (one shown), and a shaft 63. The shaft 63 of the clip 61 extends through a wall of the needle or, more preferably, its grip 11, and the spring arms 62 engage a radial groove 64 on the shaft 16 (or shaft 19). When the shaft 16 of the rake retractor is pushed or pulled relative to the needle 12, the spring arms 62 spread to permit movement of the shaft 16 past the clip 61. It will be appreciated that if the spring arms 62 are sufficiently springy, grooves are not required on the shaft 15 of the needle as the spring arms 62 will firmly hold the shaft in position.

Figure 6C:
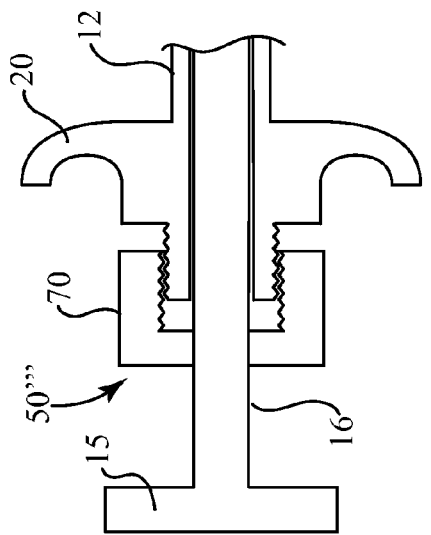

Another illustrative fixing system 50" schematically depicted in FIG. 6C includes a plastic screw 65 which extends around the shaft 16 of the rake retractor 14, and an inner thread 66 located on the grip 20 of the needle 12. When it is desired to fix the rake retractor 14 relative to the needle 12, the screw 65 is screwed into the threaded grip 20 of the needle 12. The plastic screw 65 and the inner thread 66 of the grip 20 of the needle 12 are sized to cause the plastic screw 65 to deform and tighten around the shaft 16 when the screw 65 is screwed into the thread 66, thereby fixing the locations of the needle 12 and surgical instrument 14 relative to each other. When it is desired to release the rake retractor 14, the screw 65 is unscrewed sufficiently to permit movement of the surgical instrument relative to the needle. As will be appreciated by those skilled in the art, the screw 65 may have a gripping member such as a head (not shown) to help the practitioner apply torque.

Figure 6D:
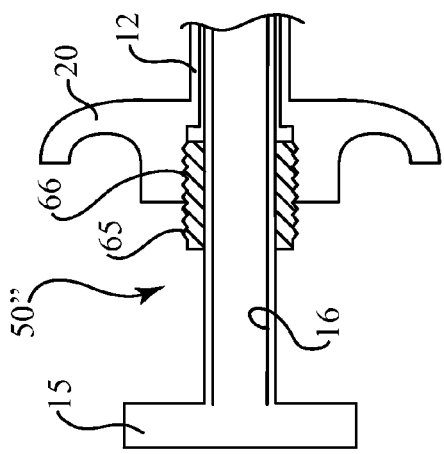

FIG. 6D schematically depicts yet another illustrative fixing system 50''' which includes a thumb screw 70 and a grip 20 of the needle 12 which includes a thread (not shown), and which is flexible or plastic. In particular, the thumb screw 70 when screwed onto the grip 20 threads causes the grip portion to clamp down on the shaft 16 of the rake retractor 14 and lock the rake retractor relative to the needle. It will be appreciated that in FIGS. 6C and 6D, the grip 20 and handle 14 are depicted as modified relative to the grip 11 and handle 15 of FIGS. 1A-C, and further that the shaft 16 in FIGS. 6C and 6D extends with a constant diameter from the needle 12 to the handle 15 whereas in FIGS. 1A-C shaft 16 is mechanically coupled to handle 15 via a proximal shaft 19 of larger diameter. Those skilled in the art will understand that these differences are illustrative of some of the variations within the purview of embodiments of the present invention, and that various handle, shaft, and grip designs may be implemented and may each employ any of various fixing means to selectively fix the rake retractor relative to the needle.

The present invention has been illustrated and described with respect to specific embodiments thereof, which embodiments are merely illustrative of the principles of the invention and are not intended to be exclusive or otherwise limiting embodiments. For instance, those skilled in the art will understand that rake retractors and surgical assemblies in accordance with alternative implementations of the present invention may use any of a variety of materials, tine designs and configurations, grips, handles, locking mechanisms, etc. Those skilled in the art will similarly understand that various aspects or features of embodiments disclosed hereinabove may be combined, such as the various tine ends (e.g., spoon-shaped, ball-tipped, etc.), tine curvatures (e.g., angular bend (s); smooth, continuous arc; straight, etc.), and shaft designs (e.g., straight; angular bend(s); smooth, continuous arc, etc.). Further, those skilled in the art will understand in view of the foregoing that all the tines of a given rake retractor within the purview of embodiments of the present invention need not have the same tine ends, tine curvatures, or other design features; that is, at least one tine may have one or more design features different from those of another tine.

Accordingly, although the above description of illustrative embodiments of the present invention, as well as various illustrative modifications and features thereof, provides many specificities, these enabling details should not be construed as limiting the scope of the invention, and it will be readily understood by those persons skilled in the art that the present invention is susceptible to many modifications, adaptations, variations, omissions, additions, and equivalent implementations without departing from this scope and without diminishing its attendant advantages. It is further noted that the terms and expressions have been used as terms of description and not terms of limitation. There is no intention to use the terms or expressions to exclude any equivalents of features shown and described or portions thereof. Additionally, the present invention may be practiced without necessarily providing one or more of the advantages described herein and/or that may be realized in some embodiments thereof. It is therefore intended that the present invention is not limited to the disclosed embodiments but should be defined in accordance with the claims that follow.

What is claimed is:

1. A surgical method, comprising:
obtaining a surgical assembly having (i) a hollow needle with a sharp distal end and an outer diameter between 2.0 mm and 3.0 mm, and (ii) a rake retractor having a shaft that extends through said hollow needle, said shaft having a central axis, said rake retractor being movable relative to said hollow needle and including at a distal end of said shaft at least three elongated tines, each tine having a first end mechanically coupled to the distal end of the shaft and an opposite free end, each tine being mechanically biased toward an open position wherein the free ends of the tines fan out relative to each other in different angular displacements with respect to the central axis of the shaft, and when said distal end of said hollow needle extends over said tines in a closed position, said tines are forced by said distal end of said hollow needle to collapse relative to each other against the mechanical bias of the tines toward and into said closed position;

with said tines of said rake retractor in the closed position, using said sharp distal end of said hollow needle to puncture the skin of said patient and insert a distal portion of said surgical assembly into a cavity of said patient;

moving said rake retractor forward relative to said needle to cause said tines to extend out of said needle and to automatically fan out relative to each other into said open position due to the mechanical bias of said tines;

moving said tines of said rake retractor to manipulate tissue within the patient; and moving said needle forward relative to said rake retractor to cause said tines to collapse relative to each other to said closed position within said needle, wherein said sharp distal end of said hollow needle has an outer surface which contacts the skin of the patient during puncture of the skin of the patient, and an inner surface which directly contacts a plurality of said tines during forward movement of the needle relative to the tines to cause the tines to collapse relative to each other within said needle.

2. The surgical method according to claim 1, further comprising moving said tines to retract an object in the cavity.

3. The surgical method according to claim 1, further comprising withdrawing said surgical assembly from said patient through the puncture formed in the skin of the patient upon inserting the surgical assembly into the patient, and allowing the puncture wound to heal independently of stitching.

4. The surgical method of claim 1, wherein:
in the closed position, the tines are substantially straight and parallel, and in the open position, respective proximal portions of the tines lie substantially within a plane, and respective distal portions of the tines extend substantially perpendicular to the plane.

5. The surgical method of claim 1, wherein:
the at least three tines include five tines, and in the closed position, the tines are operably disposed in a generally closed-packed configuration.

6. The surgical method of claim 1, wherein the hollow needle has an outer diameter sized such that a wound formed from the hollow needle puncturing skin of a patient is capable of being closed independent of stitching.

7. The surgical method of claim 1, wherein the tines of the rake retractor have respective proximal portions that lie substantially within a common plane in the open position as well as respective distal portions that are bent relative to the common plane in the open position.

8. The surgical method of claim 7, wherein the proximal portions of the tines fan out over a circular sector in the open position.

9. A surgical method, comprising:
a) obtaining a hollow needle having an outer diameter between 2.0 mm and 3.0 mm and a sharp distal end, and a rake retractor having a rake shaft which extends through the hollow needle and has a central axis, said rake retractor also having at least three tines at a first end of the rake shaft, each tine being mechanically biased toward an open position wherein the free ends of the tines are spaced apart from one another in different displacements with respect to the central axis of the rake shaft, and the rake retractor being moveable relative to the hollow needle;
b) inserting a distal portion of the hollow needle into skin of a patient using the sharp distal end, the insertion made with the tines of the rake retractor in a closed position inside the hollow needle;
c) moving the rake retractor and the needle relative to one another such that the rake retractor extends out of the needle and the tines fan out relative to each other to an open position due to the mechanical bias of said tines; and
d) moving the needle forward relative to said rake retractor such that the rake retractor is disposed in the closed position within the needle, wherein the needle has an inner surface which directly contacts a plurality of the tines and causes the tines to close together against the mechanical bias of the tines during forward movement of the needle relative to the rake retractor toward the closed position within the needle.

10. The surgical method of claim 9, further comprising maneuvering the tines to contact an object beneath the skin.

11. The surgical method of claim 9, further comprising adjusting the needle to cause the tines to contact an object beneath the skin.

12. The surgical method of claim 9, further comprising contacting an object with the rake retractor.

13. The surgical method of claim 9, wherein the hollow needle has an outer diameter sized such that a wound formed from the hollow needle puncturing skin of a patient is capable of being closed independent of stitching.

14. The surgical method of claim 9, wherein the tines of the rake retractor have respective proximal portions that lie substantially within a common plane in the open position as well as respective distal portions that are bent relative to the common plane in the open position.

15. The surgical method of claim 14, wherein the proximal portions of the tines fan out over a circular sector in the open position.

* * * * *